(12) United States Patent
Mantelmacher

(10) Patent No.: US 7,771,487 B2
(45) Date of Patent: Aug. 10, 2010

(54) ANTI-SLIP ATTACHMENT AND DRAINAGE SYSTEM FOR PROSTHETICS

(76) Inventor: H. Lee Mantelmacher, 3704 Ashley Way, Owings Mills, MD (US) 21117

( * ) Notice: Subject to any disclaimer, the term of this patent is extended or adjusted under 35 U.S.C. 154(b) by 638 days.

(21) Appl. No.: 11/496,707

(22) Filed: Jul. 31, 2006

(65) Prior Publication Data

US 2007/0032883 A1 Feb. 8, 2007

Related U.S. Application Data

(60) Provisional application No. 60/704,237, filed on Aug. 1, 2005.

(51) Int. Cl.
*A61F 2/80* (2006.01)
(52) U.S. Cl. ....................................................... 623/34
(58) Field of Classification Search .............. 623/32–37
See application file for complete search history.

(56) References Cited

U.S. PATENT DOCUMENTS

| | | | |
|---|---|---|---|
| 5,653,766 A | 8/1997 | Naser | |
| 5,728,170 A * | 3/1998 | Becker et al. | 623/37 |
| 6,645,253 B2 | 11/2003 | Caspers | |
| 6,793,682 B1 | 9/2004 | Mantelmacher | |

* cited by examiner

*Primary Examiner*—Bruce E Snow
(74) *Attorney, Agent, or Firm*—Ober / Kaler; Royal W. Craig

(57) ABSTRACT

An anchoring system for a transtibial or transfemoral (above or below the knee) prosthesis. A gel liner is inserted into a socket, and the liner has a dual-strap attachment system including an upper strap and buckle attached upwardly to the liner and passing out through the socket, and a lower strap attached distally to the liner. The liner also has a port attached at a lower distal end for introducing a vacuum into the liner and for evacuating fluids (sweat) therefrom. To accomplish the foregoing, an annular centering puck is attached at the distal end of the socket (at the aperture), the puck having a generally concave side in communication with the aperture for seating the liner therein. The centering puck is formed with a dual passage there through that passes both a vacuum tube and lower strap outward from the liner to exterior of the socket. A vacuum pump is coupled to the vacuum tube, and the liner is securely anchored in the socket by total contact induced by the vacuum force of the pump, and further secured by the first strap and buckle inserted through the socket and fastened to the second strap (passing out through the puck and inserted through the buckle, tightened, and closed upon itself to form a suspension fit which prevents lateral, pivotal and proximal shift.

15 Claims, 8 Drawing Sheets

ANTI-SLIP ATTACHMENT AND DRAINAGE SYSTEM FOR PROSTHETICS

CROSS-REFERENCE TO RELATED APPLICATION(S)

The present application derives priority from U.S. Provisional Patent Application No. 60/704,237 filed: Aug. 1, 2005.

BACKGROUND OF THE INVENTION

1. Field of the Invention

The present invention relates to prostheses and, more particularly, to an anti-slip anchoring system with drainage feature that securely anchors a suction liner with a top-side and lower lanyard-type attachment to prevent extraneous motion for above-the-knee and below-the-knee amputation patients, and which drains moisture from sweat to improve comfort without sacrificing stability.

2. Description of the Background

There are a variety of different types of prosthetic devices for patients that have had either transfemoral (above-knee) or transtibial (below the knee) amputation. Typically, post-operative prosthetic devices for either type of amputation patients begin with a liner, which is rolled on to the residual limb. The liner is a soft, stretchy material that acts as an interface with the prosthesis.

Once the liner is on, the residual limb then slides into a hard socket. This socket is specially made to fit and can be made out of a variety of materials.

The hard socket for a transfemoral prosthesis has a knee joint connected to it, and the more natural the movement of the knee the better. Transtibial prostheses have no knee joint. In both cases (with or without a knee joint) there typically is an aluminum or carbon fiber tube to which a foot module is connected. There are a number of difficult goals for the design of transfemoral and/or transtibial prostheses (above & below the knee). For one, it is very important that the socket be securely fitted to the limb and secured in place. Stability is a common problem as many existing anchoring systems use a single attachment point to hold the residual limb in place, and this typically leads to extraneous pivoting, rotation and shift during ambulation. Moreover, it is important to be able to adjust the anchoring system periodically because the mass of the limb may change significantly over the course of a day. The limb tends to change size (swell or contract) depending on use, temperature, etc. Still another goal is to minimize or evacuate moisture from within the liner. The liner is a rubber sheath and promotes heavy sweating, especially when the patient takes part in physical activities (running, etc.) that induce sweating. With most prosthetic devices the patient needs to remove the prosthesis periodically and simply pour the sweat out. This is not a convenient solution.

U.S. Pat. No. 5,653,766 to Naser issued Aug. 5, 1997 shows a prosthetic device 20 having a generally cylindrical socket 24 with an opening for receiving an amputated limb. The socket 24 is closed at the other end, and is mounted on a bendable knee joint. Once the limb is properly received within the socket 24, straps 38 are adjusted so that a secure fit is achieved. This essentially uses a radial pressure-fit imposed by tightening the two belts. However, this tends to squeeze the limb unevenly and adds to discomfort. Moreover, the radial pressure tends to pop the limb out of the socket over the course of a day.

Another well-known ICEX® Socket System uses a combination lanyard and pin kit as a docking and locking mechanism. The socket has a distal pin that docks with the prosthesis. A lanyard is connected to the liner through a slot in the bottom of the socket. The lanyard is pulled to allow the patient's residual limb, which is enclosed in the silicone liner, to be drawn into the socket by the lanyard. The lanyard is then anchored to the front of the socket. The lanyard has the advantage of allowing for adjustment of position within the ICEX Socket. If the limb changes position because of volume change and the distal migration of the limb into the socket, the prosthesis can easily be adjusted by the lanyard to compensate. The lanyard method of donning the socket also significantly reduces pain directly related to the donning process with a pin-locking mechanism. However, it has been found that many amputees lack the room for, are unable to tolerate, or have difficulty engaging the distal pin. Others complain of pain associated with engagement of the pin.

There are a number of Asuspension" type sockets that eliminate the pin. U.S. Pat. No. 6,645,253 to Caspers issued Nov. 11, 2003 shows a suction system that employs a vacuum pump to impart suction to the liner, the vacuum pump doubling as a shock absorber for the artificial limb. Commercially, this is known as the Harmony® System. FIG. 1 is a perspective view of the Harmony System, which pulls air from the sealed socket 12 and also evacuates moisture (sweat) buildup. A nonporous polyurethane liner (not shown) is fitted over the residual limb and is inserted in the socket 12. A vacuum pump 30 is attached via a connector block 20 beneath the socket 12 to create a vacuum force which is coupled by a tube to the socket, thereby evacuating air and sealing it to the residual limb. This provides a total-contact hypobaric suction equal weight distribution socket liner which tacks up to the skin of the residual limb and provides total contact with the limb. Research has shown that patients lose six to twelve percent of their residual limb volume in the course of a day, leaving the limb smaller than the prosthetic socket. With the Harmony System vacuum-assisted technology, the residual limb size stays the same and the prosthesis fits better all day long. The existing Harmony System as described in the '253 patent is a suspension system which uses a liner with no mechanical connection between the liner and socket, but also suggests a mechanical interlock such as a distal pin on the liner (similar to that of the ICEX Socket System) that fits into the socket. Again, many amputees lack the room for, are unable to tolerate, or have difficulty engaging a distal pin. The suspension embodiment remains susceptible to extraneous up and down motion, pivoting, rotation and shift during ambulation. It would be greatly advantageous to supplement the suspension Harmony System to include a more stable lanyard-type fixation feature to eliminate extraneous movement. Unfortunately, this is difficult with the suspension Harmony System because the suction liner is suspended over an evacuation nozzle at the bottom of the socket that evacuates moisture (sweat) outside of the socket. This leaves little room for supplemental attachment features.

U.S. Pat. No. 6,793,682 to Mantelmacher discloses a "Sure-fit Prosthetic Attachment System" (known commercially as the KISS® System) for a transfemoral and/or transtibial prosthesis, comprising a liner for enveloping an amputee limb. The liner has a buckle suspended toward the upper end, and a corresponding strap fixedly attached on the bottom end of the liner. The anchoring system also includes a containment socket for seating the liner. The containment socket has a pair of slots there through at positions corresponding to the buckle and strap of the liner, respectively. To apply the anchoring system, the patient first applies the liner to his/her limb. The liner is then inserted into the socket with the fastening strap and buckle protruding out through the respective slots. The fastening strap is then threaded up through the buckle (running upward along the side of the socket) and are inserted there through. The patient pulls down on the strap and it works by pulley action to draw the liner down into the socket until the liner is securely seated in the socket. When fully seated, the fastening strap is secured to itself by Velcro. The foregoing forms a suspension which holds the prosthesis on. Moreover, the fastening straps through slots absolutely prevent lateral shift as well as rotation. On the other hand, the patient need only readjust the Velcro closure to adjust the position of the limb within the socket. Thus, if the limb changes position because of volume change and the distal migration of the limb into the socket, the prosthesis can easily be adjusted to compensate. Despite the advantages, the '682 patent could not heretofore be used with a locking suction liner (liner pin mating with socket) as with the Harmony System, and the '682 patent provides no drainage solution in and of itself. Integrating a drainage system into a prosthetic attachment is no easy matter without compromising comfort or stability. Just the slightest discontinuity or protruberance inside the liner can be unbearable to a patient over time.

It would be greatly advantageous to incorporate a moisture evacuation feature into the KISS® attachment system, and further to combine the KISS® dual-lanyard-type attachment and its advantages (stability, comfort, ease of application and adjustment, etc.) with the added stability of a vacuum-assisted locking suction liner as in the Harmony System to provide unmatched comfort and stability against extraneous up and down motion, pivoting, rotation and shift during ambulation.

SUMMARY OF THE INVENTION

Accordingly, it is an object of the present invention to provide a dual-lanyard prosthetic anchoring system with integral moisture evacuation feature It is another object to combine a dual-lanyard (KISS® type) attachment system with a locking suction liner and (Harmony® type pump) to provide a dual-lanyard vacuum-assisted suction, plus top-side and lower mechanical lanyard-type attachments to prevent all extraneous up and down motion, pivoting, rotation and shift.

It is another object to combine the benefits of the existing suspension-type Harmony System with vacuum-assisted suction locking liner and moisture evacuation, with a dual-lanyard mechanical fastening strap running upward along the side of the socket to prevent extraneous up and down motion, pivoting, rotation and shift during ambulation.

It is still another object to provide a prosthetic anchoring system as described above that remains easy to put on, and to readjust/tighten the fit of the liner in the socket from a sitting position.

In accordance with the foregoing object, the present device comprises an anchoring system for a transfemoral and/or transtibial prosthesis, comprising a flexible liner for enveloping an amputee limb, and a hard socket for receiving the liner and limb. The socket generally conforms to the limb and is formed with a distal aperture. The liner has a first attachment assembly including a first strap attached proximate the upper end of the liner, and a buckle attached to the strap. The first strap passes outward through the socket via a slot formed in the upper socket.

A second attachment assembly is attached to the lower distal end of the liner, the second attachment assembly including second strap anchored at the end of the liner and threaded outward through the lower socket. The second strap extends outward from the lower socket and carries spaced closures (such as opposing hook-and-loop sections) which allow it to be inserted through the buckle borne by the first strap and then fastened back onto itself, thereby securing the liner to the socket via a double-lanyard attachment.

The foregoing is similar to the above-described U.S. Pat. No. 6,793,682 to Mantelmacher, but the present invention additionally introduces moisture evacuation and/or vacuum suction into the liner in a novel way. This is accomplished by attaching a threaded port to the distal lower end of the liner (thereby providing a fluid port through the liner), screwing a port nipple into the port, and attaching a drainage/vacuum tube to the port nipple. The drainage/vacuum tube is threaded outward through the lower socket along with the second strap to thereby provide fluid communication into/from the liner for drainage of fluid and/or introduction of a vacuum into the liner. The junction of the port nipple to the port also provides a convenient attachment point of the second strap to the liner.

The lower distal end of the socket (which is open at the aperture) is attached to an annular centering puck. Thus, the top of the puck is exposed interiorly of the socket to the liner and the periphery and bottom of the puck lie outside the socket. The top of the puck is formed with a generally concave recess for seating the liner and providing clearance for the port and port nipple. The centering puck is formed with a dual passage there through that passes from the concave face outward through the circular periphery of the centering puck to pass both the vacuum tube and second strap outward from the liner to exterior of the socket. A connector block is attached to the centering puck beneath the socket, and any of a variety of artificial limbs/knees/feet with or without dampening mechanisms may be attached to the connector block.

In accordance with one embodiment of the invention, the vacuum tube may be fastened to the artificial limb and equipped with a distal one-way valve for simple drainage of fluid from the liner.

Alternatively, a vacuum pump such as shown and described in the '253 patent to Caspers may be attached to the connector block, and the vacuum tube attached to the vacuum pump to introduce vacuum suction into the liner thereby evacuate air as well as fluid (sweat) out of the liner, thereby sealing the liner to the patient's residual limb and avoiding fluid build-up. This way, the liner is securely anchored to the residual limb in the socket by total contact induced by the vacuum force of the pump, and further secured by the dual-lanyard formed by the first strap and buckle inserted through the socket and fastened to the second strap which form a suspension fit that prevents lateral, pivotal and proximal shift. The vacuum pump may also serve as a shock absorber for the artificial limb.

BRIEF DESCRIPTION OF THE DRAWINGS

Other objects, features, and advantages of the present invention will become more apparent from the following detailed description of the preferred embodiment and certain modifications thereof, in which.

DETAILED DESCRIPTION OF THE PREFERRED EMBODIMENTS

The present invention is a prosthetic attachment system for transfemoral (above-knee) or transtibial (below knee) amputees that incorporates a moisture evacuation feature into a dual-lanyard attachment system, and optionally adds a vacuum-assisted locking suction liner to provide unmatched comfort and stability against extraneous up and down motion, pivoting, rotation and shift during ambulation.

Figure 1:
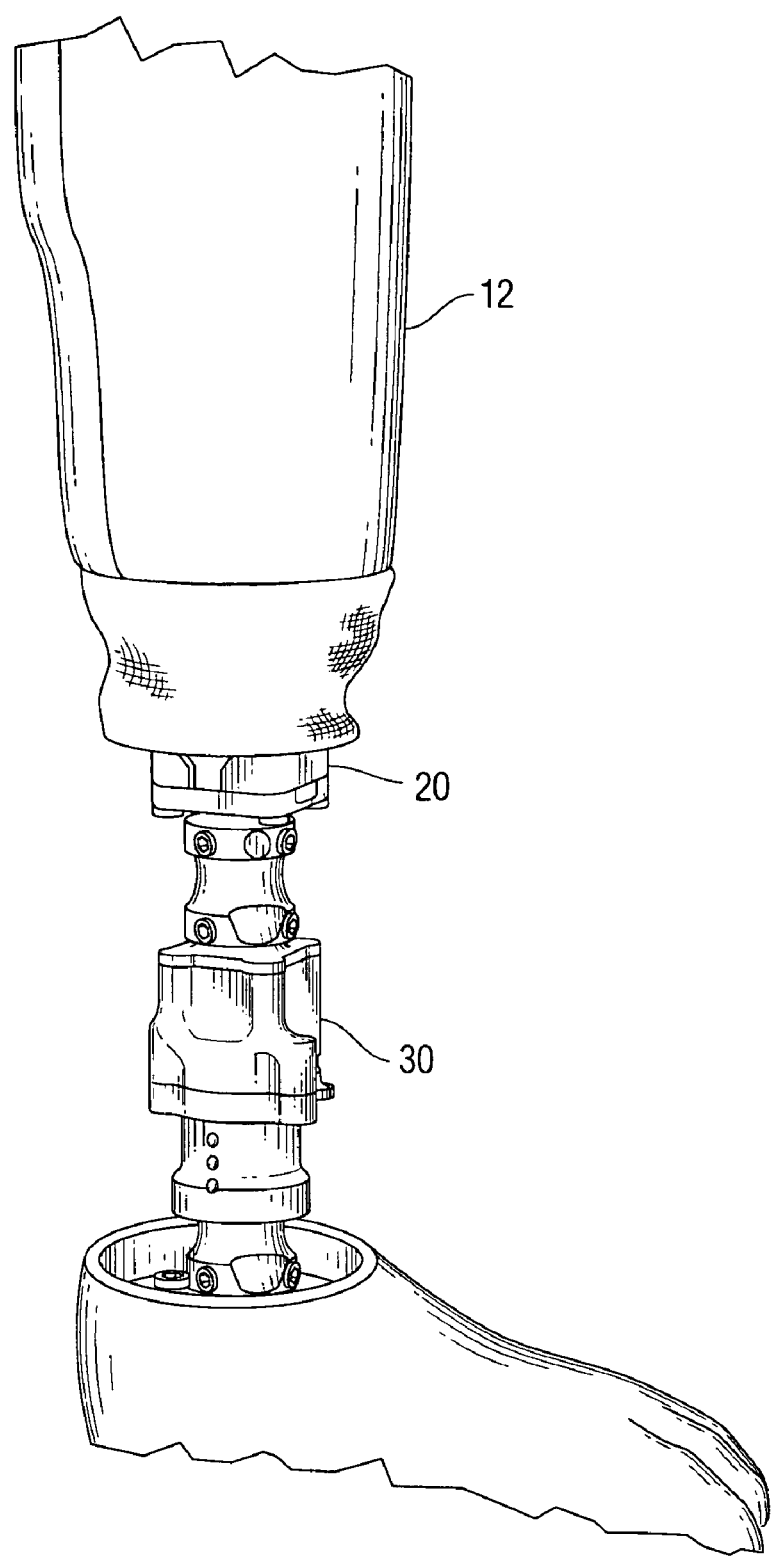
FIG. 1 is a perspective view of the prior art Harmony System.
Figure 2:
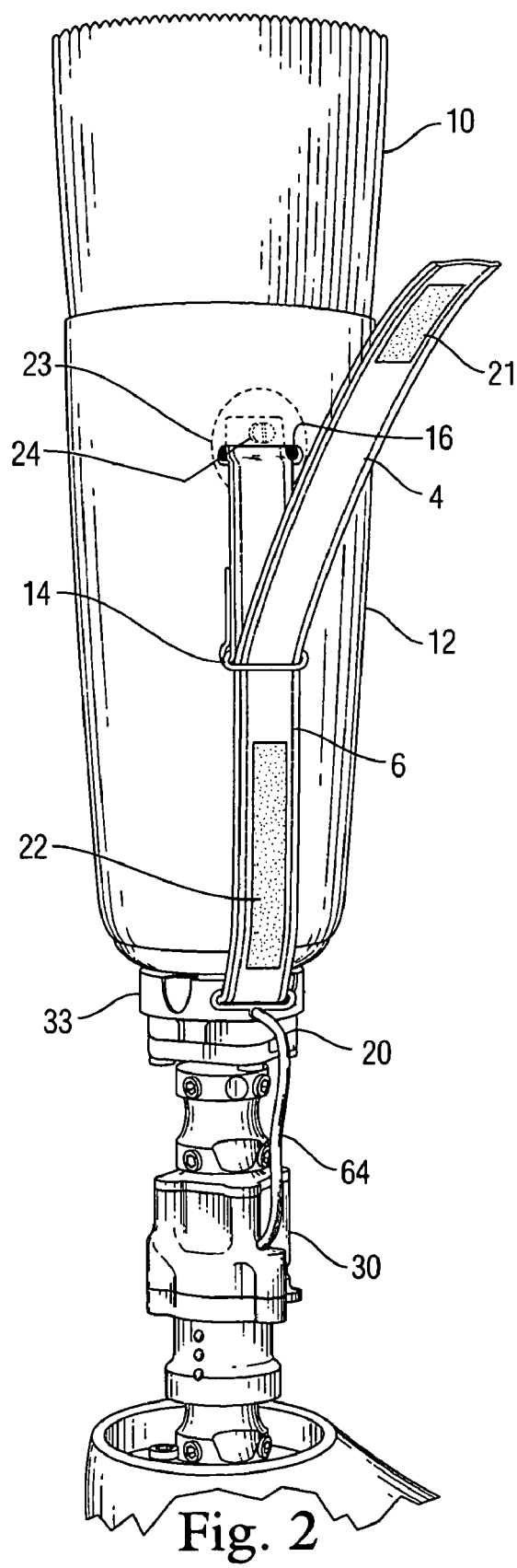
FIG. 2 is a perspective view of the prosthetic attachment system according to the present invention.

FIG. 2 is a perspective view of the prosthetic attachment system according to a first embodiment of the present invention, which integrates a moisture evacuation feature into a dual-lanyard attachment system, and also adds a vacuum-assisted locking suction liner. Toward this latter goal the attachment system incorporates some conventional elements of the above-described Harmony System such as a hard socket 12, nonporous gel liner 10 fitted over the residual limb and inserted in the socket 12, and a vacuum pump 30 attached via a connector block 20 beneath the socket 12 for drawing air as well as fluid out of the liner, thereby creating a vacuum that seals the liner against the residual limb.

The present invention also incorporates a dual-lanyard mechanical attachment in conjunction with the vacuum-assist, and the dual-lanyard attachment is integrated in such as way as to maintain the fluid-tight junction at the bottom of the liner and socket. Thus, to allow the drawing of fluid (air and moisture), a hole is cut in the distal end of the liner 10, and this is equipped with a port 42 into which a port insert assembly 65 is attached (both obscured but described in more detail in FIG. 5). The port insert assembly 65 allows connection of a vacuum tube 64 that is ultimately connected to vacuum pump 30 (see FIG. 6) for evacuation of fluid (air and moisture) and creating the vacuum suction between liner 10 and socket 12.

To this is added upper and lower attachment assemblies that rely on strap-anchors 4, 6 both attached to the liner 10 and threaded out through the socket 12, the attachment assemblies being adjustably secured together to anchor the liner 10 in the socket 12. More specifically, a lower strap anchor 6 threads out from the distal end of the liner 10 through a unique centering puck 33. An upper strap 4 (a 2-5" length of Nylon or Dacron braided strap) is pivotally attached at one end to the upside of liner 10 by a grommet 24 secured to a reinforcement plate 23, plate 23 being a flexible plastic member that is sewn and/or bonded peripherally onto the liner 10 at an upper outside position as shown. Presently, the grommet 24 comprises two screw-together sections having 1" flanges which sandwich the plate 23 and upper strap 4 together. A buckle 14 is attached to the other end of upper strap 4, and a short section of strap may extend from the buckle 14 to provide the user with a finger grip to pull the strap 4 up and liner 10 down.

In addition, a lower strap 6 is approximately a 16" length of braided Nylon or Dacron strap attached at one end to the bottom of liner 10.

Figure 5:
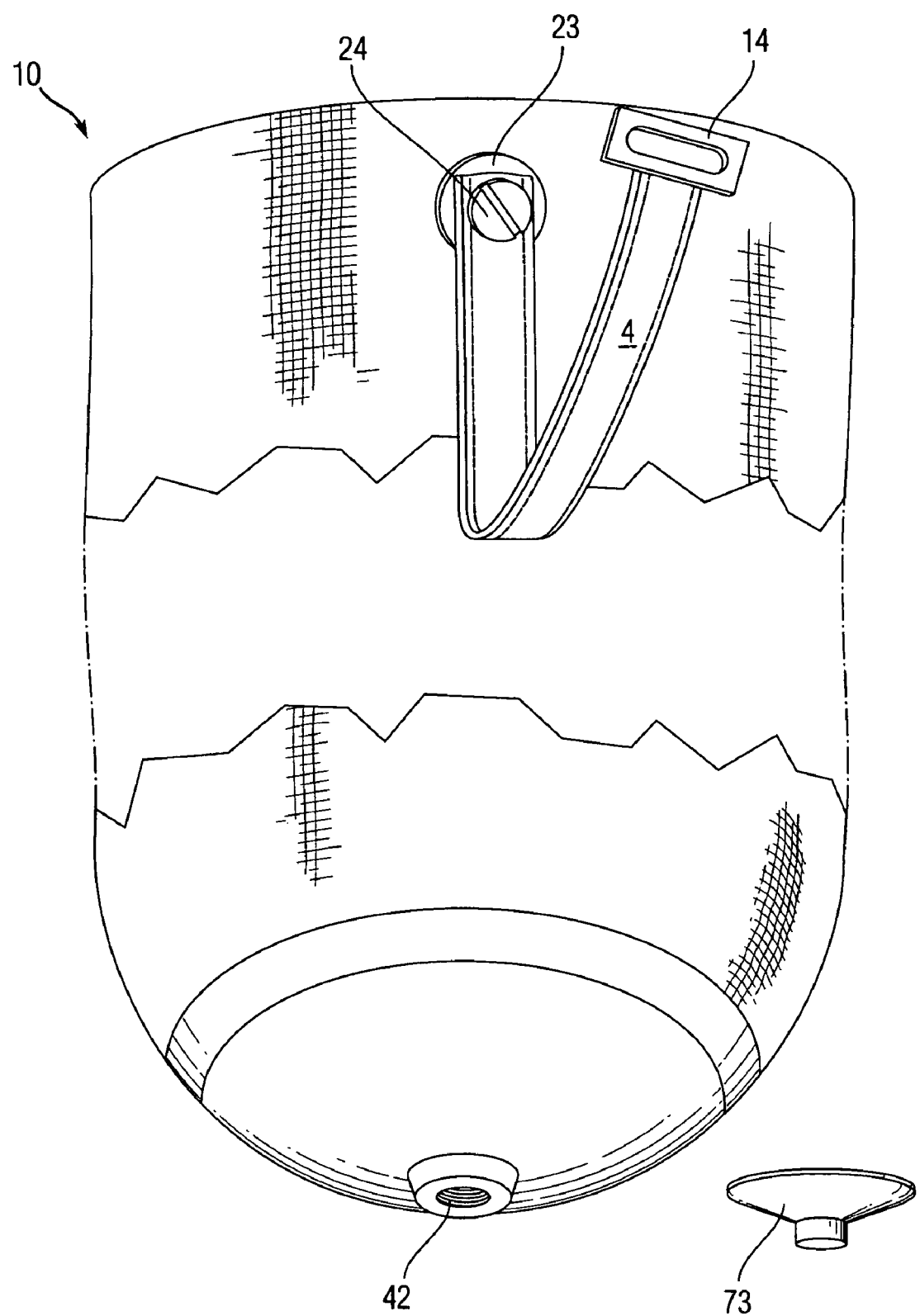
FIG. 5 is a close-up perspective view of the liner 10.

As best seen in FIG. 5, liner 10 is equipped with a threaded port 42 at the bottom end which is a threaded metal screw-socket embedded and epoxied and/or sewn, or otherwise fixedly attached to the distal end of the liner 10.

Figure 3:
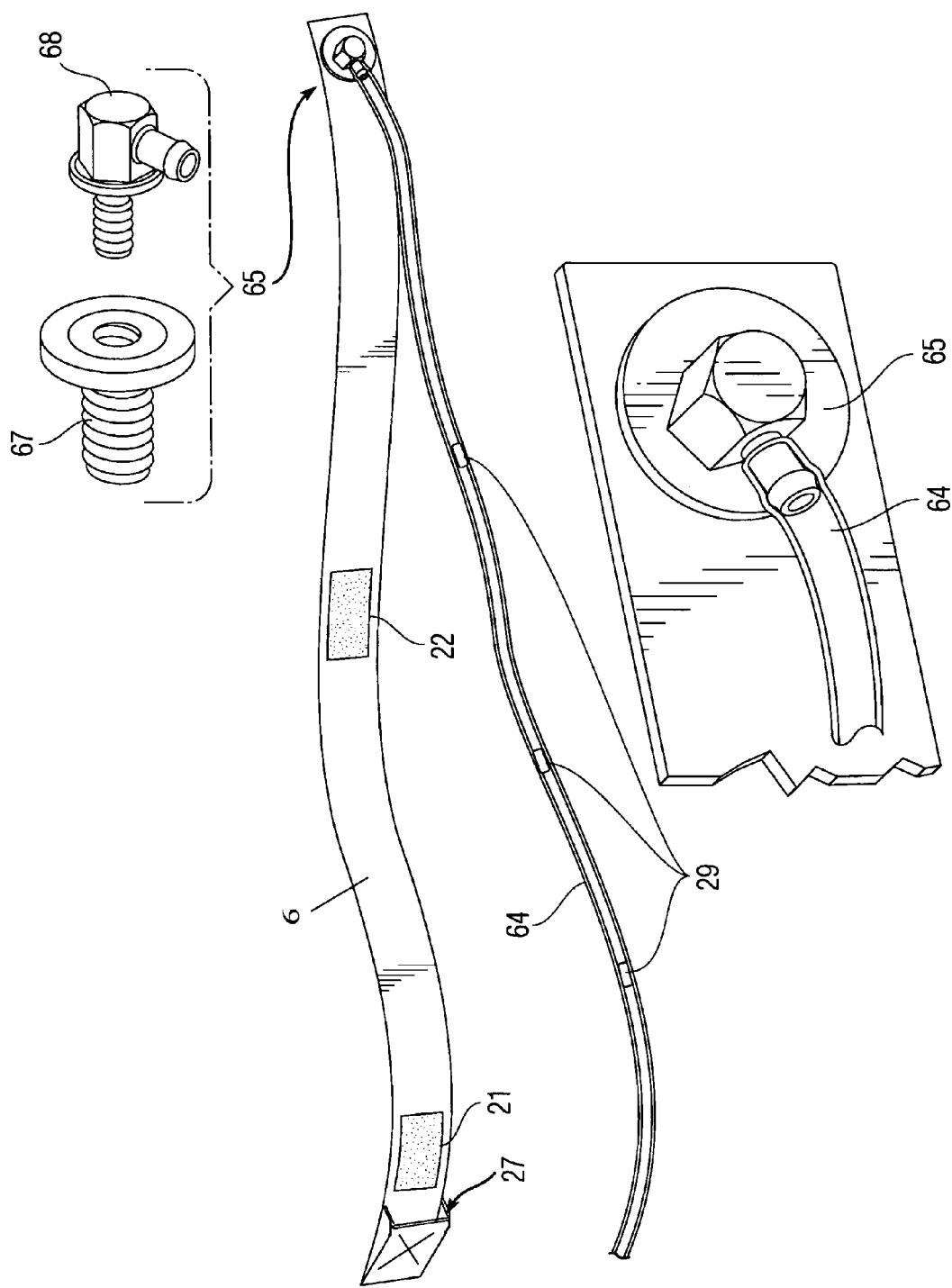
FIG. 3 is a close-up isolated view of the lower strap 6.

As shown in FIG. 3, a port insert assembly 65 is passed through the strap 6 and is screwed into the threaded port 42 to anchor the strap 4 thereto.

Referring back to FIG. 2, the lower fastening strap 6 has a section 21 of hook-and-loop material attached to the distal end, and a mating section 22 of hook-and-loop material running lengthwise along its mid-section for attaching strap 6 onto itself around the buckle 14 of the upper strap 4.

The liner 10 fits within a molded socket 12, the socket 12 being seated in and attached to a centering puck 33, the centering puck 33 being attached to a connecting block 20, which is in turn connected to vacuum pump 30 beneath the socket 12. The vacuum pump 30 is in fluid communication through a vacuum/evacuation tube 64 to the interior of liner 10 for evacuating air therefrom as well as moisture (sweat). For transfemoral patients, the vacuum pump 30 is adapted for attachment to a conventional, bendable knee joint (a variety of which are presently available). For transtibial patients, the vacuum pump 30 is adapted for attachment to a conventional prosthetic leg (a variety of which are presently available). In both cases the manner in which the vacuum pump 30 is connected will generally depend on how much residual limb remains. Where there is less residual limb there is more space to mount the vacuum pump 30 inline between the connecting block 20 and artificial limb or knee joint as seen in FIG. 2. On the other hand, a transtibial prosthesis (below knee) may not leave sufficient room to mount the vacuum pump 30 as shown in FIG. 2, and an offset mounting (relative to the knee joint) may be required.

Socket 12 is generally a conventional socket formed of rigid and/or flexible plastic that is vacuum formed. The socket 12 is a custom-fitted component that is made in a conventional manner of a copolymer plastic, plastic polypropylene, polyester, acrylic/epoxy resin. The socket 12 may be vacuum formed or thermoformed by heating the plastic material and forming it over a mold.

Figure 6:
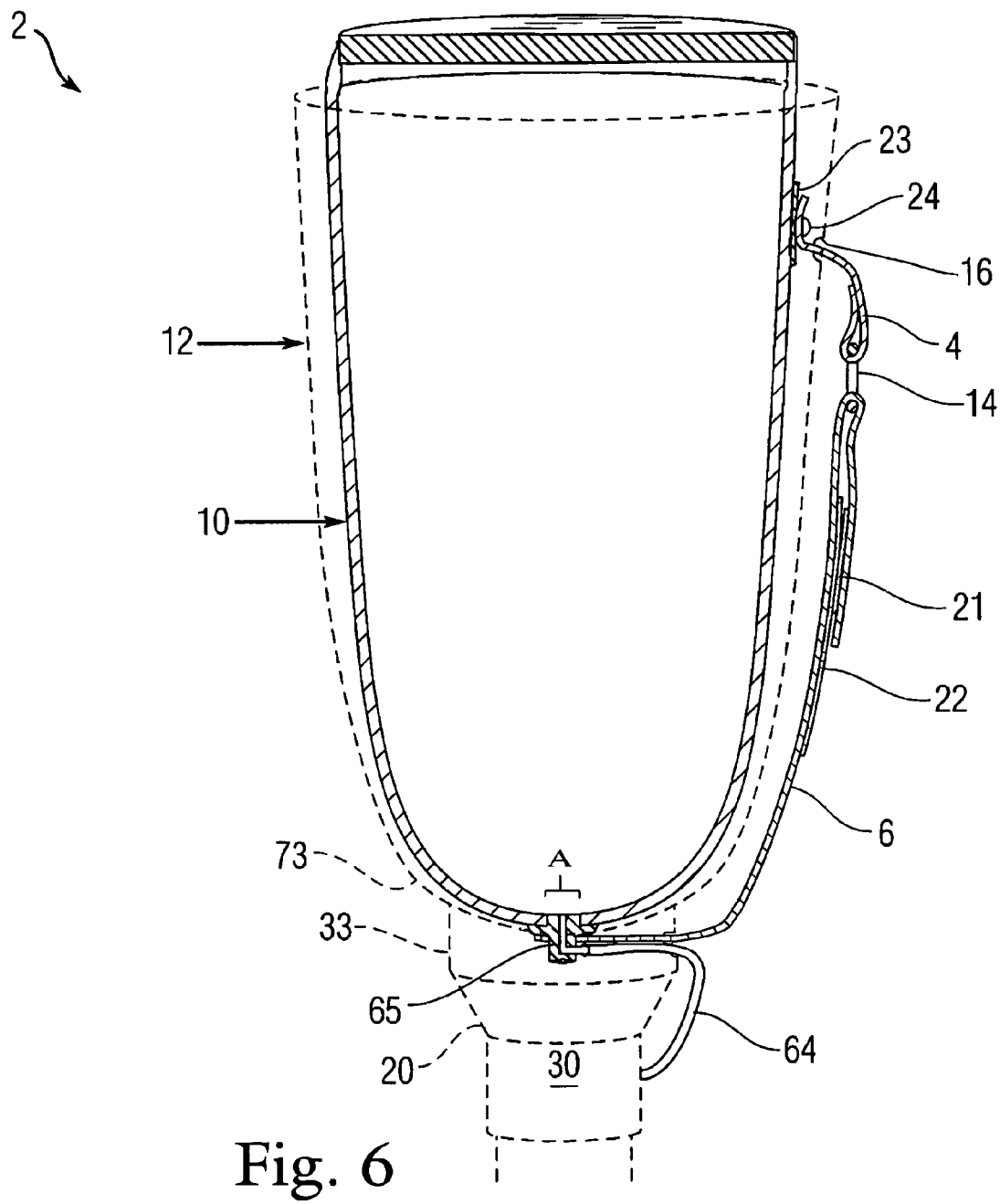
FIG. 6 is a perspective illustration showing the method of attaching the sure-fit prosthetic anchoring system 2 according to the present invention.

As seen in FIG. 6 the socket 12 is formed with at least one pass-through slot 16 upwardly along the outside for passing upper strap 4. At least one pass-through slot 16 is required, although two or more pass-through slots may be positioned upwardly along the opposing sides of the socket 12 to provide an adjustment feature. Whether a single slot 16, a pair, or a series, the slots are spaced with respect to the liner 10 inserted therein so that they are aligned with the upper strap 4. Specifically, when the liner 10 is fully inserted at least one pass-through slot 16 should be even with the grommet-post 24 on liner 10. If present, other pass-through slots may be positioned slightly above or below for adjustment. This allows the tethered buckle 14 to be inserted directly through a selected slot 16 (as appropriate) from inside the socket 12 to outside, such that downward tension on strap 4 anchors the grommet-post 24 directly against the slot.

The lower distal end of socket 12 is formed with a central aperture (A) about which puck 33 is mounted, and this allows the lower strap 6 to pass outwardly through the puck 33. The lower fastening strap 6 has a section 21 of hook-and-loop material at the distal end, and a mating section 22 of hook-and-loop material running lengthwise along its mid-section. In addition, the lower fastening strap 6 is preferably formed with a distal pocket (described below) to allow temporary insertion of the end of vacuum tube 64 in order to conjoin the tube 64 and strap 6 for easier insertion through the puck 33, after which the vacuum tube 64 can be dislodged.

In use, the patient would first apply liner 10 to limb. The liner 10 is then inserted into the socket with lower fastening strap 6 (and integral vacuum/evacuation tube 64) threaded through centering puck 33 out through slots 36, 37, and upper strap 4 with buckle 14 passing out through upper slot 16. The lower fastening strap 6 is then threaded up through the protruding buckle 14 and downwardly, and the strap 6 is pulled tight until the liner 10 is securely seated in the socket 12 atop puck 33. The fastening strap 6 is secured onto itself by joining the sections 21, 22 of hook-and-loop material. The foregoing forms a suspension which holds the prosthesis on and absolutely prevents lateral movement, pivotal shifting, and rotation. On the other hand, the simple Velcro®-attached strap 6 allows for convenient adjustment of the position of the limb within the socket 12.

FIG. 3 is a close-up isolated view of the lower attachment assembly which combines the lower strap 6 with a vacuum/evacuation tube 64, and port insert assembly 65. More specifically, the lower fastening strap 6 is joined to a vacuum/evacuation tube 64 at port insert assembly 65. An enlarged illustration of the port insert assembly 65 is shown at bottom and, as will be described, port insert assembly 65 is in fluid communication with the liner 10 for evacuation of moisture there from. An exploded illustration of the port insert assembly 65 is shown at top. The port insert assembly 65 includes a right-angle tube-connector 68 which is screwed or welded centrally into a tapped and threaded flat-head bolt 67. This forms a passage from the inside of liner 10 through the flat-head bolt 67 and outward through the right-angle tube-connector 68. The end of fastening strap 6 is punched with a hole such that it can be inserted onto the threaded flat-head bolt 67, becoming sandwiched between the flat-head bolt 67 and liner 10. A conventional vacuum/evacuation tube 64 is connected to the nipple of the right-angle tube-connector 68. The combination of the fastening strap 6 with vacuum/evacuation tube 64 and port insert assembly 65, all in one integral unit greatly simplifies the overall design. Two additional design features help to contribute to usability of this lower attachment assembly.

For one, as seen in FIG. 3, the distal end of the lower strap 6 is preferably formed with a pocket 27 as shown that allows the end of the vacuum/evacuation tube 64 to be tucked inside. This makes it much easier to pass the vacuum/evacuation tube 64 (together with the lower fastening strap 6) out through centering puck 33 via slots 36, 37 as described above. Secondly, one or more additional small patches of hook-and-loop material may be spaced along the vacuum/evacuation tube 64 to bind it to lower strap 6, taking up slack and avoiding a loose-hanging tube 64.

The above-described threaded flat-head bolt 67 screws into the threaded port 42 in liner 10 (as described below with regard to FIG. 5) for transferring a vacuum from pump 30 into liner 10 as well as evacuation of moisture from liner 10, the moisture primarily being sweat that flows out from the liner 10 through the flat-head bolt 67 and outward through the right-angle tube-connector 68 through vacuum/evacuation tube 64.

The entire above-described port insert assembly 65 is seated in a centering puck 33 that is in turn attached at the bottom of the socket 12 as shown in FIG. 2, and both the evacuation tube 64 and fastening strap 6 pass outward through the side of the centering puck 33. The puck 33 may literally be attached to the bottom of the socket 12 around the aperture therein, or alternatively, the socket 12 may be formed with a depression at the bottom for receiving and seating the puck 33 inside. In the former case the puck 33 may be attached beneath the socket 12 in a number of ways. For example, through-bores may be formed axially through the puck 33 to allow screw-attachment through the socket 12 into the connector block 20 beneath the socket 12. Alternatively, the through-bores 34 may be eliminated and the centering puck 33 instead formed with a downwardly threaded hub for screw-attachment to the connector block 20 beneath the socket 12. In the latter case (puck 33 seated inside socket 12) the socket 12 need not have a distal aperture but must be formed with a slot to allow sidelong passage of the second strap 6 and vacuum tube 64.

Figure 4:
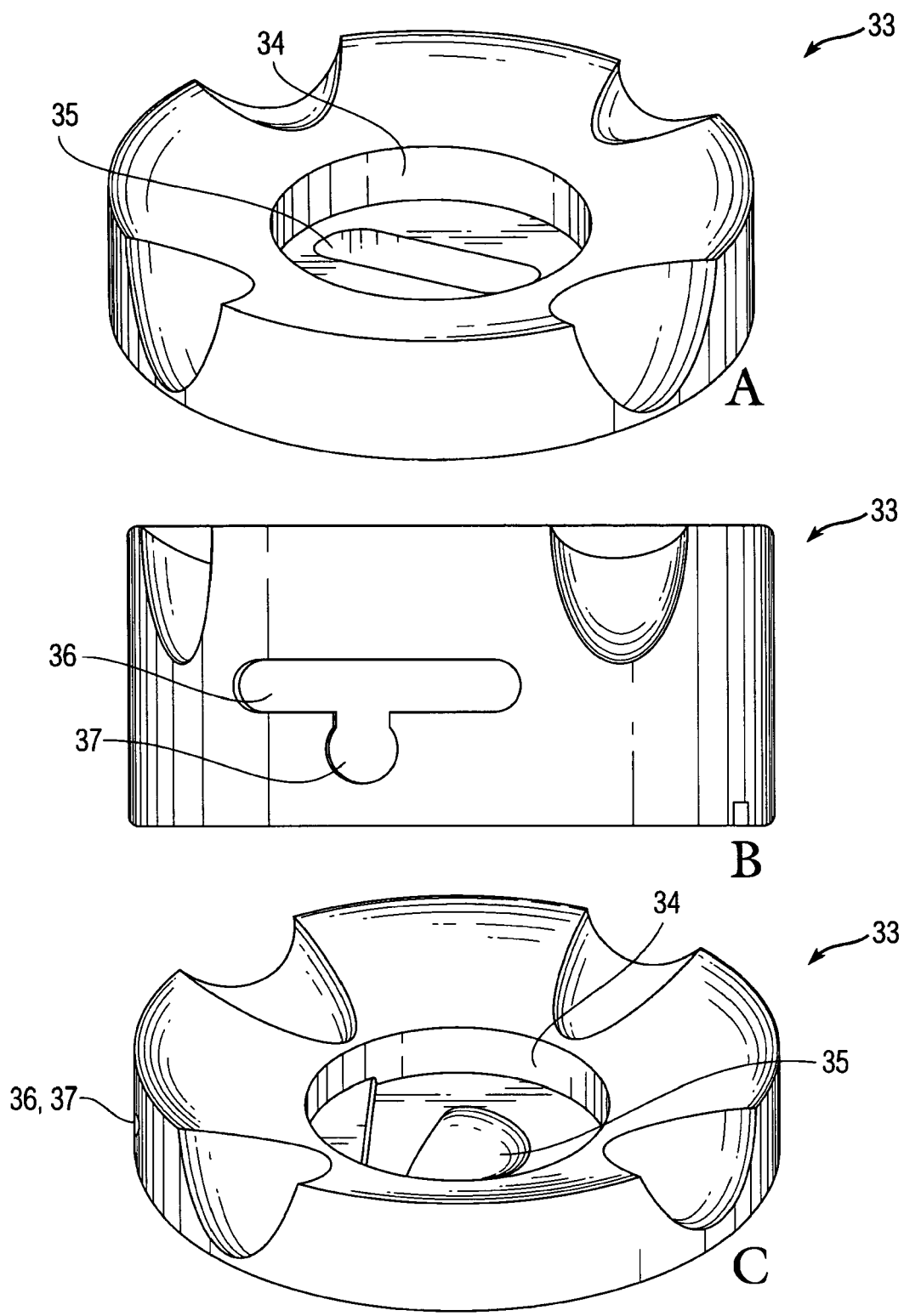
FIG. 4 is a composite top perspective view (at A), front view (B), and rotated top perspective view (C), respectively, of the centering puck 33 which is attached internally to the bottom center of the socket 12.

FIG. 4 is a composite top perspective view (at A), front view (B), and rotated top perspective view (C), respectively, of the centering puck 33 which is attached externally to or seated in the distal end of the socket 12. The centering puck 33 is a generally puck-shaped member preferably formed of Delrin®, aluminum, or other sturdy material. Centering puck 33 is formed with a concave recess 34, the recess 34 leading into a deeper alcove 35. The concave upper surface helps to seat and center the socket 12. The alcove 35 is semi-circular (on one side as best seen at C) leading to a more pronounced indentation in the center for accommodating the port insert assembly 65 which protrudes downwardly from the liner 10. The alcove 35 continues out through the front side of puck 33 through a generally T-shaped aperture including a transverse slot 36 through which the lower fastening strap 6 is passed, and a circular aperture 37 through which the vacuum/evacuation tube 64 is passed. The transverse slot 36 and circular aperture 37 may be integrally formed through puck 33 as shown.

FIG. 5 is a close-up perspective view of the liner 10. Liner 10 is largely a standard transfemoral or transtibial suspension liner designed for amputees with amputations along the length of the tibia or femur. There are a variety of commercially-available suspension liners which will suffice, provided that they afford good suspension independent of volume fluctuations and provide a comfortable anatomical fit. These liners are typically formed of silicone or a gel blend with a fabric shell. For present purposes the liner 10 is additionally equipped with a threaded port 42 at the bottom end for screw-insertion of the flat-head hex bolt 66 of the above-described port insert assembly 65.

In accordance with the present invention, the otherwise conventional liner is modified by tethering the buckle 14, via upper strap 4, to the outwardly facing side of the liner 10. A hole is formed through the lower distal end of liner 10, and port 42 is secured to the bottom of liner 10 at the hole. Strap 4 is secured to the liner 10 by first sewing and/or gluing the reinforcement pad 23 peripherally to the shell of the liner 10, and then passing a grommet-post 24 through the tip of the upper strap 4 and through the pad 23, thereby pivotally anchoring strap 4 thereto. Strap 4 is a short length (approximately 6") of braided Nylon or Dacron strap that is looped around one side of a rectangular buckle 14, thereby suspending buckle 14 approximately 3-5" downward from post 24. The buckle 14 is a simple rectangular stirrup-type stainless fixture. It should be understood that alternate embodiments are possible without departing from the scope and spirit of the invention, the point being that the tethered buckle 14 must be suspended a short distance beneath grommet-post 24. If desired, a short length (approximately 1-2") of additional strap material (not shown) may be attached to the opposing side of buckle 14 in a like manner and extended therefrom to provide a finger-grip to facilitate insertion of the strap 4 and buckle 14 through the upper slot 16 in socket 12.

In addition to the upper strap 4 with buckle 14, the lower strap 6 passes out through the transverse slot 36 of centering puck 33, and upper strap 4 with buckle 14 passes out through upper slot 16. The lower fastening strap 6 is then threaded up through the protruding buckle 14 and downwardly, and the strap 6 is pulled tight until the liner 10 is securely seated in the socket 12 atop puck 33. The fastening strap 6 is secured onto itself by joining the sections 21, 22 of hook-and-loop material.

One significant but optional improvement is a breathable foam insert 73 that fits inside the port 42 and yet provides an internal cushion (inside liner 10) to the residual limb. Foam insert 73 must be breathable to allow input of vacuum suction and drainage of moisture through port 42. For this purpose, an open-fiber polyester mattress foam material such as RELY™ fiber by Carpenter Co. (which features an antimicrobial treatment) is well-suited, although other foams will suffice. The foam insert 73 may be shaped as a simple annular plug that fits inside port 42, but preferably employs a T-shaped cross-section as shown to give the residual limb some padding inside liner 10. Without the foam insert 73 patients will tend to wear socks, but socks cause sores in a vacuum system such as this. The foam insert 73 completely eliminates sores and allows most patients to continue wearing their prosthesis all day without taking it off to void moisture or otherwise.

FIG. 6 is a cross-section that better-illustrates the method of attaching the sure-fit prosthetic anchoring system 2 according to the present invention. To apply the anchoring system 2, the patient first applies the liner 10 to his/her residual limb. The liner 10 is then partially inserted into the socket 12 until lower fastening strap 6 and conjoined vacuum tube 64 can be threaded through the slot 36 in centering puck 33 and on outward. In addition, the upper fastening strap 4 and buckle 14 are passed outward through slot 16. The lower fastening strap 6 and vacuum tube 64 are separated, and the strap 6 is threaded up through the buckle 14 (strap 6 running upward along the side of the socket 12) and is inserted there through. The patient pulls down on the distal end of lower strap 6 which works by pulley action to draw the liner 10 down into the socket 12 until the liner 10 is securely seated in the socket 12. When fully seated, the lower fastening strap 6 is secured to itself by joining the sections 21, 22 of hook-and-loop material.

The foregoing forms a suspension which holds the prosthesis on. Moreover, the fastening strap 6 through puck 33 forms a first anchoring point, and the upper strap 4 through upper slot 16 forms a second anchoring point, the combination of the two anchoring points serving to absolutely prevent lateral movement, pivotal and proximal shift, and rotation.

The vacuum tube 64 is then attached to the vacuum pump 30.

The dual-lanyard attachment in combination with the vacuum suction induced by vacuum pump 30 forms a suspension that opposes the vacuum suction, thereby providing the most robust prosthetic anchor known to be available It holds the prosthesis on and absolutely prevents lateral movement, pivotal shifting, and rotation. If the limb changes position because of volume change or distal migration of the limb into the socket, the prosthesis can easily be adjusted by dispelling the vacuum, and adjusting straps 4, 6 to adjust the position of the limb within the socket 12. Once the limb is properly received within the socket 12 and the straps 4, 6 are appropriately adjusted so that a secure fit is achieved, the patient then is able to ambulate using the prosthetic device.

Figure 7:
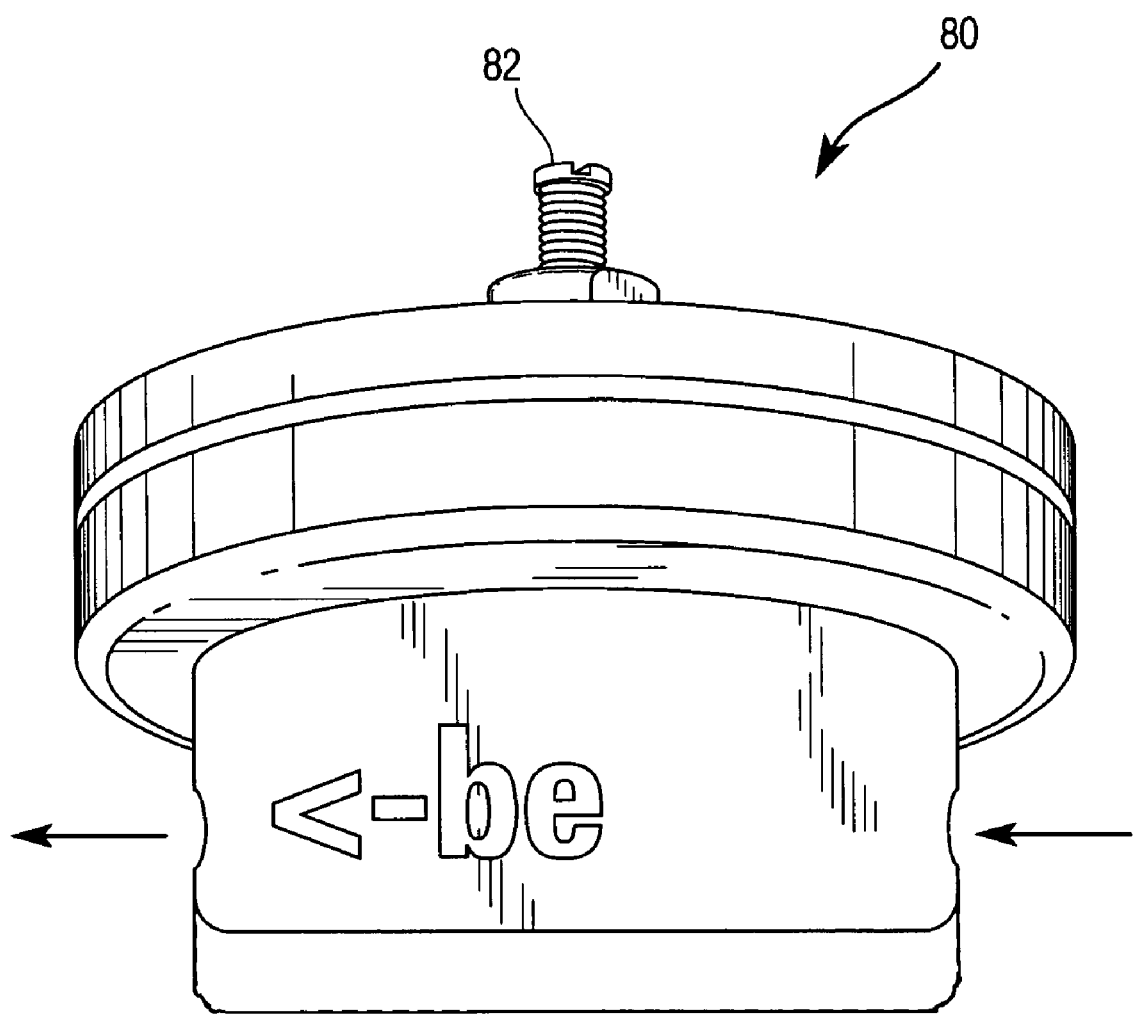
FIG. 7 is a rotary adjust pressure regulator suited for use with the present invention.

The vacuum pump 30 may be a mechanical or motor-driven pump, as used and sold commercially with the Harmony® System and as further described in U.S. Pat. No. 6,645,253 summarized previously. In this case the vacuum pump 30 is connected via vacuum/evacuation tube 64 to induce a vacuum into the liner 10, as well as to extract moisture therefrom. It is noteworthy that the existing vacuum pump 30 of the Harmony® System provides a fixed vacuum to cause the residual limb (with or without sock coverings) to be drawn firmly against the inner surface of the liner 10. In this regard the vacuum pump 30 has been tested and found to maintain a vacuum in the range of 15-25 inches of mercury, which is quite high for some patients. It is much more convenient to provide a means for regulating the vacuum supplied by vacuum pump 30 to any pressure within a range of from 0-25 inches of mercury, and for this purpose a regulator may be provided in-line with evacuation tube 64 to allow control over the vacuum pressure. The present inventor has found that a rotary adjust pressure regulator is well-suited for this purpose, such as a Beswick Engineering VPD regulator as shown in FIG. 7. The rotary adjust inline regulator 80 of FIG. 7 is placed inline along vacuum/evacuation tube 64 and allows convenient manual regulation by set screw 82 of the pressure supplied by vacuum pump 30 anywhere within a range of from 0-25 inches of mercury. The preferred Beswick unit is approximately 1"×1" by ½" in size and can be bracket-mounted external to the vacuum pump 30 or mounting block 20 for convenient access. The amputee or caretaker simply then sets the regulator 80 to cause the vacuum pump 30 to apply vacuum through the vacuum/evacuation tube 64 to the liner 10.

It should now be apparent that the above-described prosthetic anchoring system will draw the liner 10 down onto the residual limb, causing a hypobarically-controlled suspension and locking the residual limb into the socket and liner 10 without causing swelling of the residual limb. There is hybobarically-induced total contact of the residual limb with the liner 10 and socket (that is, there is no open chamber between the residual limb and the liner 10 within the socket which would draw on the residual limb). As the volume of the residual limb changes during the day due to weight-bearing pressures or otherwise, the regulator 80 may be adjusted to adjust the vacuum pump 30 to draw the residual limb firmly against the liner 10 (within the socket) and thus compensate for said changes.

Figure 8:
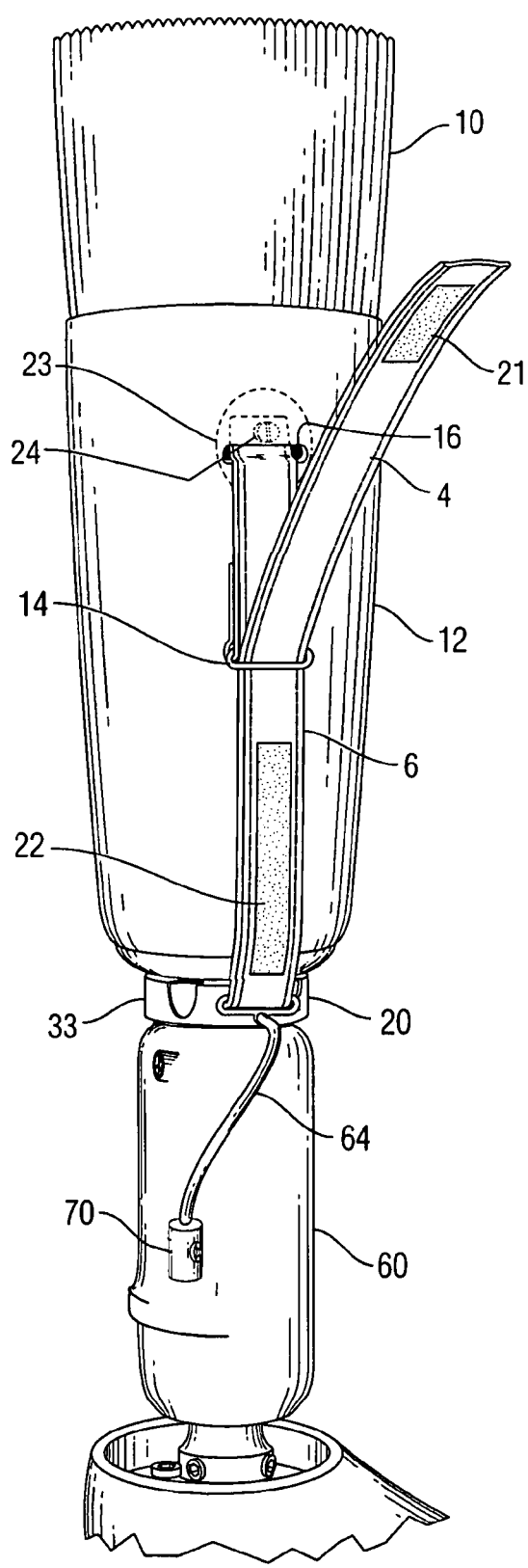
FIG. 8 is a perspective view of the prosthetic attachment system according to another embodiment of the present invention attached to a conventional prosthetic limb and adapted for fluid evacuation only, with no vacuum-assisted suction imparted to the liner 10.

Alternately, the present invention may be adapted for attachment to a more conventional prosthetic limb without a vacuum pump and thereby adapted for fluid evacuation only, relying on the above-described dual-lanyard fixation but with no vacuum-assisted suction imparted to the liner. FIG. 8 is a perspective view of an alternate embodiment of the prosthetic attachment system which does not employ a vacuum pump 30 as described above. In this case, the socket 12 or puck 33 is attached directly to a conventional prosthetic limb 60 or by way of an intermediate shock absorber in the same manner of attachment to vacuum pump 30 as described above. Without a vacuum pump there is nothing to impart a vacuum into liner 10 and so nothing to couple the vacuum tube 64 to. It is used for fluid drainage purposes only and is preferably equipped with a one-way valve 70 at its distal end to eject fluid without introducing fluid or air. A commercially available Tetra™ one-way valve is well-suited for this purpose and prevents water from "back-syphoning" into the tube 64

In all the above-described embodiments the prosthetic anchoring system 2 described herein increases the stability of the liner anchor using the combined top-side and lower attachments to prevent all extraneous up and down motion, pivotal and proximal shift, and rotation. It avoids the need for distal pin locks, and yet allows the patient to easily anchor the liner 10 in the socket 12, and to easily readjust/tighten the fit of the liner 10 in the socket 12 from a convenient sitting position. Moreover, it permits fluid evacuation and optionally allows a vacuum suction liner without sacrificing comfort and stability.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. An anchoring system for a prosthesis, comprising:
a flexible liner having an interior volume for enveloping an amputee limb, said liner having a port at a lower distal end opening through the liner into said interior volume;
a port insert attached in the port of said liner, said port insert having a one way drainage valve in fluid communication with said port for evacuating fluid out of the interior volume of said liner without backflow;
a hard socket for receiving said flexible liner; and
a centering puck, the centering puck comprising an annular member formed with a generally concave side conforming to and in communication with the socket for seating thereon, and a passage leading from said recess outward through said puck.

2. The anchoring system for a prosthesis according to claim 1, wherein said centering puck is formed of any one of Delrin™, aluminum, and titanium.

3. The anchoring system for a prosthesis according to claim 1, wherein said passage has a generally T-shaped cross-section.

4. The anchoring system for a prosthesis according to claim 1, further comprising:
a first attachment assembly including a first strap attached proximate an upper end of said liner; and
a second attachment assembly including a second strap attached distally at the port insert on said liner.

5. An anchoring system for a prosthesis, comprising:
a flexible liner for enveloping an amputee limb, said liner also having a port at a lower distal end;
a first attachment assembly including a first strap attached proximate an upper end of said liner, and a buckle attached to said strap;
a second attachment assembly including a second strap attached distally at the port of said liner, said second strap having spaced fasteners thereon for fastening said second strap onto itself around said buckle;
a port insert attached in the port of said liner;
a tube attached to said port insert and in fluid communication with an interior of said liner;
a hard socket for receiving said flexible liner, said socket having a first slot there through at a position corresponding to the first strap, and a constricted end for seating said amputee limb in said liner; and
a centering puck attached at the constricted end of said socket, said puck having a generally concave topside for seating the liner, a recess in said concave topside for accommodating said port insert, and a passage from said recess trough said puck for passing both said vacuum tube and second strap outward from said liner exterior to said socket.

6. The anchoring system for a prosthesis according to claim 5, further comprising a connector block attached to said puck beneath said socket.

7. The anchoring system for a prosthesis according to claim 5, further comprising a connector block attached to said socket beneath said puck.

8. The anchoring system for a prosthesis according to claim 5, further comprising a vacuum pump coupled to said vacuum tube for generating a vacuum to evacuate air out of the liner, thereby sealing said liner to a residual limb.

9. The anchoring system for a prosthesis according to claim 5, further comprising a one-way valve coupled to said vacuum tube for evacuating fluid out of the liner without backflow.

10. The anchoring system for a prosthesis according to claim 8, wherein said liner is securely anchored in said socket by total contact induced by the vacuum force of said pump, and is further secured by the first strap, buckle and second strap.

11. The anchoring system for a prosthesis according to claim 5, wherein said first strap is inserted through the first slot of the socket and the second strap passes out through said puck and is inserted through the buckle, tightened, and closed upon itself to form a suspension fit which prevents lateral, pivotal and proximal shift.

12. The anchoring system for a prosthesis according to claim 8, further comprising a pressure regulator, said vacuum pump being coupled to said vacuum tube via said pressure regulator for generating a regulated vacuum to evacuate air out of the liner, thereby sealing said liner to a residual limb.

13. The anchoring system according to claim 5, wherein the groove in said centering puck comprises a transverse groove to pass said second strap, and an adjoined circular aperture to pass said vacuum tube.

14. The anchoring system according to claim 5, wherein the fasteners on said second strap comprise mating sections of hook and loop material.

15. The anchoring system according to claim 5, wherein the first strap comprises a distal pocket for insertion of said tube to conjoin said tube during insertion through said puck.

* * * * *